United States Patent
Wilson et al.

(10) Patent No.: US 10,481,121 B2
(45) Date of Patent: Nov. 19, 2019

(54) MEMS SENSOR

(71) Applicant: Cirrus Logic International Semiconductor Ltd., Edinburgh (GB)

(72) Inventors: Paul Wilson, Linlithgow (GB); Karthikeya Kodur, Edinburgh (GB)

(73) Assignee: Cirrus Logic, Inc., Austin, TX (US)

( * ) Notice: Subject to any disclaimer, the term of this patent is extended or adjusted under 35 U.S.C. 154(b) by 0 days.

(21) Appl. No.: 15/904,737

(22) Filed: Feb. 26, 2018

(65) Prior Publication Data

US 2018/0246052 A1 Aug. 30, 2018

Related U.S. Application Data

(60) Provisional application No. 62/464,137, filed on Feb. 27, 2017.

(30) Foreign Application Priority Data

Mar. 20, 2017 (GB) .................................. 1704396.9

(51) Int. Cl.
*H03F 3/45* (2006.01)
*G01N 27/22* (2006.01)
(Continued)

(52) U.S. Cl.
CPC ............. *G01N 27/228* (2013.01); *G01D 5/24* (2013.01); *G01D 5/2417* (2013.01); *H03F 3/187* (2013.01);
(Continued)

(58) Field of Classification Search
CPC .......... H03F 1/181; H03F 1/183; H03F 1/185; H03F 1/187; H04R 5/04
(Continued)

(56) References Cited

U.S. PATENT DOCUMENTS 4,794,349 A 12/1988 Senderowicz et al.
9,083,288 B2 7/2015 Thomsen
(Continued)

FOREIGN PATENT DOCUMENTS

EP 0375195 A2 6/1990
EP 0415080 A2 3/1991
(Continued)

OTHER PUBLICATIONS

Combined Search and Examination Report of the UKIPO, Application No. GB1704396.9, dated Sep. 22, 2017.
(Continued)

*Primary Examiner* — Steven J Mottola
(74) *Attorney, Agent, or Firm* — Jackson Walker L.L.P.

(57) ABSTRACT

This application relates to methods and apparatus for operating MEMS sensors, in particular MEMS capacitive sensors ($C_{MEMS}$) such as a microphones. An amplifier apparatus (300) is arranged to amplify an input signal ($V_{INP}$) received at a sense node (104) from the MEMS capacitive sensor. An antiphase signal generator (201; 304) generates a second signal ($V_{INN}$) which is in antiphase with the input signal ($V_{INP}$) and an amplifier arrangement (105; 305) is configured to receive the input signal ($V_{INP}$) at a first input and the second signal ($V_{INN}$) at a second input and to output corresponding amplified first and second output signals. This converts a single ended input signal effectively into a differential input signal.

28 Claims, 6 Drawing Sheets

(51) Int. Cl.
　　　*G01D 5/241*　　(2006.01)
　　　*H03F 3/187*　　(2006.01)
　　　*H04R 19/00*　　(2006.01)
　　　*G01D 5/24*　　(2006.01)
　　　*H04R 3/06*　　(2006.01)

(52) U.S. Cl.
　　　CPC ..... *H03F 3/45179* (2013.01); *H03F 3/45475* (2013.01); *H03F 3/45645* (2013.01); *H03F 3/45941* (2013.01); *H04R 3/06* (2013.01); *H04R 19/005* (2013.01); *H03F 2201/3212* (2013.01); *H03F 2203/45418* (2013.01); *H03F 2203/45424* (2013.01); *H04R 2499/11* (2013.01)

(58) Field of Classification Search
　　　USPC .......................... 330/174; 381/120, 121, 122
　　　See application file for complete search history.

(56) References Cited

U.S. PATENT DOCUMENTS

| | | |
|---|---|---|
| 2011/0216920 A1 | 9/2011 | Yamamoto et al. |
| 2012/0121106 A1 | 5/2012 | Henriksen |
| 2015/0131813 A1 | 5/2015 | Kim et al. |
| 2015/0137834 A1 | 5/2015 | Steiner |
| 2016/0352294 A1 | 12/2016 | Nicollini et al. |

FOREIGN PATENT DOCUMENTS

| | | | | |
|---|---|---|---|---|
| EP | 3331160 A1 * | 6/2018 | ............... | H03F 1/26 |
| WO | 2005076466 A1 | 8/2005 | | |

OTHER PUBLICATIONS

International Search Report and Written Opinion of the International Searching Authority, International Application No. PCT/GB2018/050486, dated Jun. 20, 2018.

* cited by examiner

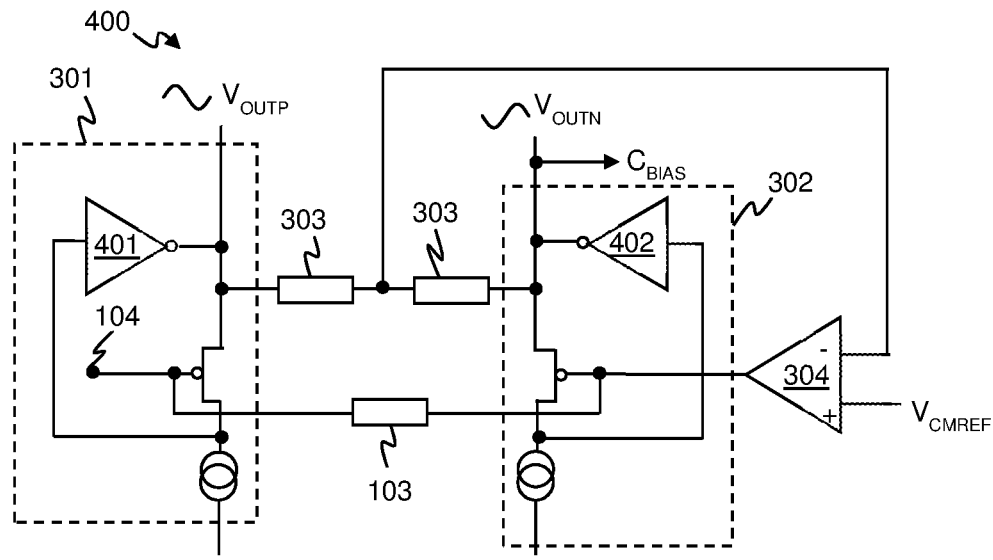
Figure 4
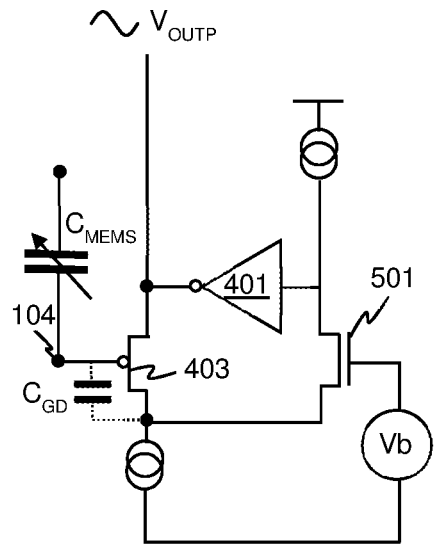 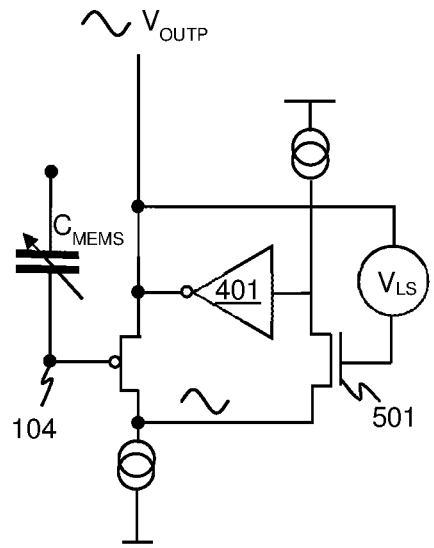
Figure 5a                        Figure 5b

MEMS SENSOR

TECHNICAL FIELD

This application relates to methods and apparatus for operation of Micro-electromechanical-system (MEMS) sensors, such as MEMS microphones, and especially to the readout and amplification of signals from MEMS sensors.

BACKGROUND

MEMS sensors, such as MEMS capacitive microphones, are becoming increasing popular, at least partly due to their small size. For instance MEMS microphones may usefully be employed on portable electronic devices such as mobile telephones or tablet computers and the like. The increasing popularity of voice control is also leading to microphones being provided on a range of devices, such as smart watches or other wearable devices or on other consumer electronics products and MEMS microphones are being usefully used on such products.

MEMS capacitive microphones typically comprise one electrode, which is moveable with respect to at least one fixed electrode in response to incident acoustic waves to form a variable capacitance, typically of the order of 1 pf or so. The moveable electrode may, for example, be supported by a flexible membrane. In use a first one of the electrodes may be biased by a relatively high stable bias voltage $V_{BIAS}$, say 12V or so in some instances, whilst the second electrode is biased to another fixed voltage $V_{REF}$, typically ground, via a very high impedance, for example, in the order of 10 GΩ. Acoustic waves incident on the capacitive transducer will cause displacement of the moveable electrode with respect to the fixed electrode, thus changing the spacing between these electrodes and hence the inter-electrode capacitance. As the second electrode of the transducer is biased via a very high impedance, these changes in capacitance cause a signal voltage to appear at the input terminal. Given the small capacitance of the MEMS sensor the input signal is relatively small and thus the signal is amplified by a low-noise amplifier arrangement.

One issue that arises for such MEMS microphones is providing sufficient dynamic range. To provide acceptable output signal levels at lower input acoustic signal level requires a certain amplifier gain. However at higher acoustic signal levels this can result in overload, where the resulting relatively large input signal magnitude exceeds the linear range of the amplifier at the input and/or output and distortion is introduced. In most cases the maximum signal level that can be amplified is limited by the power supply voltage minus headroom.

One way to deal with this problem is to use compression, where the system parameters are adjusted to effectively reduce sensitivity of the sensor based on an indication of signal amplitude, for instance the bias voltage supplied to the first electrode may be reduced. However this adds complexity and results in a variable sensitivity over the operating range.

SUMMARY

Embodiments of the present disclosure are thus directed at methods and apparatus for MEMS sensors that at least mitigate at least some of the above mentioned issues.

Thus according to one aspect there is provided an amplifier apparatus for amplifying an input signal from a MEMS capacitive sensor comprising:

a sense node for receiving the input signal;
an antiphase signal generator for generating a second signal which is in antiphase with the input signal; and
an amplifier arrangement configured to receive the input signal at a first input and the second signal at a second input and to output corresponding first and second output signals.

The amplifier apparatus may further comprising biasing circuitry for generating a bias voltage for biasing the MEMS capacitive sensor at a biasing node. In some embodiments the amplifier apparatus is configured such that the bias voltage at the bias node is modulated with a modulation signal based on the second signal. In some embodiments there is a feedback path for feeding the second signal or the second output signal back to the biasing node. The feedback path may comprise a biasing capacitor.

In some embodiments the antiphase signal generator generates the second signal based on a common-mode voltage of the first and second output signals. The antiphase signal generator may comprise a feedback amplifier configured to receive a common-mode signal indicative of a common mode voltage of the first and second output signals and a common-mode reference voltage and to drive the second signal at the second input of amplifier arrangement to keep the common mode voltage of the first and second output signals to be equal to the common-mode reference voltage. There may be first and second resistances connected in series between a first output node driven with the first output signal and a second output node driven with the second output signal, wherein the common-mode signal is derived from the midpoint of the first and second resistances. A common-mode reference generator may generate the common-mode reference voltage based on an input reference voltage. The common-mode reference generator may comprise a transistor which is a scaled replica of an input transistor of the amplifier arrangement.

In some implementations the antiphase signal generator may comprise an inverting amplifier configured to receive the input signal from the sense node.

The amplifier arrangement may comprise a first single-ended amplifier for amplifying the input signal. In some implementations there may also be a second single-ended amplifier for amplifying the second signal. Each of the first and, if present, second single-ended amplifiers may comprise a source follower or super-source follower amplifier with a class AB driver for driving the respective first or second output signal. The first amplifier may comprise an input transistor with a gate terminal connected to the sense node and a bootstrap circuit for driving a drain terminal of the input transistor in phase with the first output signal.

In some instances an input bypass switch may connect the first input of the amplifier arrangement to the second input. A clamp controller may selectively control the input bypass switch to clamp the input signal within a defined voltage range. The clamp controller may be configured to monitor the input signal against an input signal clamp limit and/or to monitor at least one of the first and second output signals against an output signal clamp limit. The apparatus may be configured to close the input bypass switch in response to a start-up control signal.

The biasing circuitry may comprise a voltage source for outputting the bias voltage and a resistance between the voltage source and the biasing node. A biasing bypass switch may provide a bypass path that bypassing the resistance between the voltage source and the biasing node. The biasing bypass switch may comprise at least one PMOS transistor. The voltage source may be configured to generate a control voltage, the control voltage being higher than the bias voltage, wherein the biasing circuitry is configured such that, in normal operation the control voltage is applied to a gate terminal of the biasing bypass switch.

Embodiments relate to an apparatus with a MEMS capacitive sensor coupled to the sense node. In some implementations the MEMS capacitive transducer is integrated with the amplifier arrangement in an integrated circuit. The MEMS capacitive sensor may be a MEMS microphone.

Aspects also relates to an electronic device comprising an amplifier arrangement as described in any of the variants above. The device may be at least one of: a portable device; a battery powered device; a communication device; a mobile telephone; a computing device; a tablet, laptop or notebook computer; a wearable device; a voice controlled device.

In another aspect there is provided an amplifier apparatus for amplifying an input signal from a MEMS capacitive sensor comprising:
   an amplifier arrangement having first and second inputs;
   wherein the first input is configured to receive the input signal and the second input is configured to receive a second signal which is in antiphase with the input signal;
   a signal generator for generating the second signal at said second input; and
   a bias source for biasing the MEMS capacitive sensor with a bias voltage;
   wherein the bias voltage is modulated based on the second signal.

A further aspect provides an amplifier arrangement for amplifying an input signal from a MEMS capacitive sensor comprising:
   a first single-ended input amplifier configured to receive and amplify the input signal as a first output signal;
   a second single-ended input amplifier configured to receive and amplify a second signal as a second output signal;
   wherein the second signal is generated by the amplifier arrangement to be in antiphase to the first signal; and
   a modulator for modulating a bias voltage applied to the MEMS capacitive sensor based on said second signal.

BRIEF DESCRIPTION OF THE DRAWINGS

To explain various aspects of the present disclosure various embodiments will now be described, by way of example only, with reference to the accompanying drawings, of which:

FIG. 4 illustrates the example of FIG. 3a in more detail;

FIGS. 5a, 5b and 5c illustrate examples of various LNA implementations without and with bootstrapping;

DETAILED DESCRIPTION

Figure 1:
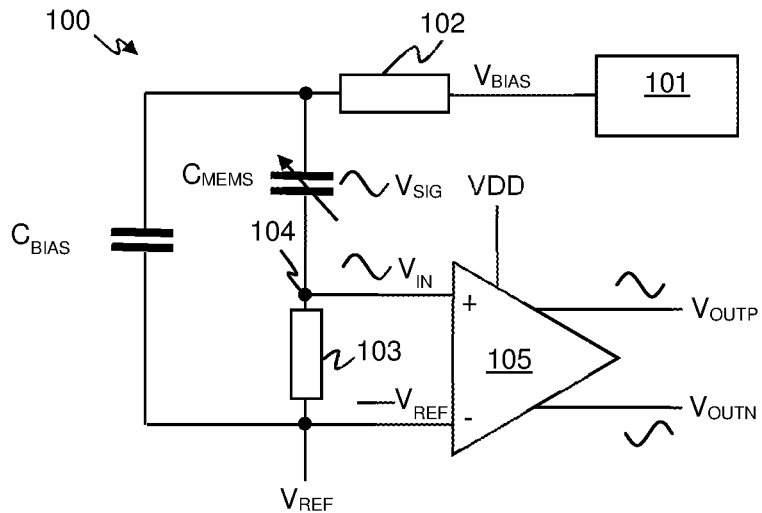
FIG. 1 illustrates one example of a MEMS sensor arrangement.

FIG. 1 illustrates one example of a MEMS sensor arrangement 100 for operation of a MEMS capacitive sensor, such as a MEMS microphone. The MEMS microphone is illustrated as a variable capacitance $C_{MEMS}$. A first electrode or plate of the MEMS sensor $C_{MEMS}$ is biased with a biasing voltage $V_{BIAS}$ from a voltage source 101. The voltage source 101 may, for instance be a charge-pump, which may boost an input voltage, to the defined bias voltage $V_{BIAS}$. The bias voltage $V_{BIAS}$ may be applied to the first electrode via filter arrangement comprising resistance 102 (for instance comprising polysilicon diodes) and a biasing capacitor $C_{BIAS}$ to provide a stable biasing voltage for the transducer.

A second plate or electrode of the MEMS capacitive transducer $C_{MEMS}$ is coupled to a reference voltage $V_{REF}$ via a high impedance element 103, which may for instance be in the order of gigaohms or so. High impedance element 103 may for instance comprise polysilicon diodes or similar.

The capacitance of the MEMS sensor $C_{MEMS}$ is typically only of the order of 1 pf or so, and so the sense signal received at a sense node 104 connected to the second plate requires local buffering/amplification. A voltage amplifier 105 may thus be arranged to generate a buffered voltage output. The amplifier 105 may present a high input impedance, so the charge on the MEMS capacitance remains constant. The voltage at a sense node 104 connected to the second plate thus varies inversely proportional to the capacitance, which itself is inversely proportional to the plate separation, so overall the detected voltage $V_{IN}$ is dependent on the displacement of the plates of the MEMS capacitive sensor $C_{MEMS}$. Pressure waves cause displacement of the plates of the MEMS capacitive sensor $C_{MEMS}$ which results in a voltage variation $V_{SIG}$ which is detected as the input voltage $V_{IN}$ from the sense node and amplified by amplifier 105.

In the example illustrated in FIG. 1 the amplifier 105 is configured to provide a differential output signal, i.e. outputs of $V_{OUTP}$ and $V_{OUTN}$ which vary inversely from one another to provide a differential voltage that varies with the input signal $V_{IN}$. The amplifier 105 thus also receives the voltage reference $V_{REF}$. Providing a differential output signal can improve noise performance by increasing the power-supply-rejection-ratio (PSRR) of the MEMS sensor arrangement. A differential output has a benefit because the maximum differential output signal is 2×Vdd minus headroom. Compared with a single ended input, single ended output LNA however, there is a noise penalty caused by the extra input device in this example.

In the arrangement illustrated in FIG. 1 the maximum input signal that can be amplified linearly is limited by the input range of amplifier 105, e.g. the power supply voltage VDD minus sufficient headroom. There is an increasing demand for microphones to be able to operate in noisy environments or environments with large low frequency components such as wind noise without distorting and thus there is a general desire to improve the linear operating range of the microphone arrangement, i.e. to improve overload performance by being able to cope with a high input sound pressure level without clipping.

The operating range of the amplifier may be increased by increasing the supply voltage but this would increase power consumption, which is undesirable, especially for portable devices which operate off battery power and where battery life is an important consideration. An increased supply voltage would also result in increased supply noise if for example a DCDC converter was used to boost the supply voltage.

Dynamic range has been extended by using the techniques of compression to vary the sensitivity of the microphone, for instance by reducing the bias voltage $V_{BIAS}$ for larger amplitude acoustic signals so as to reduce the voltage of the signal $V_{IN}$ at the sense node. However this results in the overall response of the microphone being non-linear or time-varying or subject to transient artefacts as $V_{BIAS}$ is changed which may be undesirable in some implementations.

In embodiments of the present disclosure an input voltage signal is received from the MEMS sensor and an additional signal which is in antiphase to the input signal is generated. The input signal and generated antiphase signal can be used to provide a differential output signal. In some embodiments the input signal and generated antiphase signal may be used as differential inputs, e.g. for a differential amplifier arrangement. Thus the input signal is used to provide a first output signal and a complementary second output signal that varies inversely with the first output signal is derived. In effect the single-ended input signal is converted to a differential signal with two antiphase signal components. This extends the input range of the amplifier from being equal to the supply voltage less headroom to being double the supply voltage less headroom. Thus the operating range of the amplifier is improved, without requiring any increase in supply voltage or negative impact on PSRR.

Figure 2:
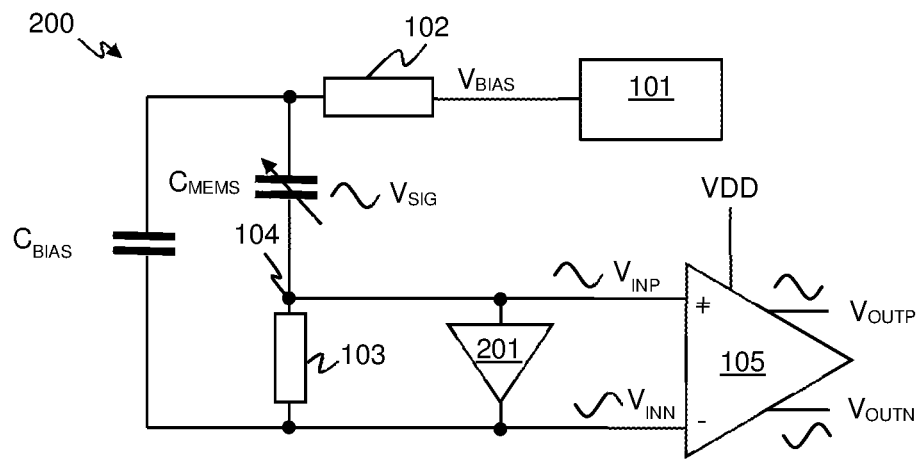
FIG. 2 illustrates a MEMS sensor arrangement according to an embodiment.

FIG. 2 illustrates an amplifier arrangement 200 according to one embodiment where similar components to those already discussed are identified by the same reference numerals. In this embodiment an antiphase signal generator is configured to generate an antiphase signal from the measurement signal at the sense node. In this embodiment the antiphase signal generator comprises an inverting amplifier 201 coupled to the sense node 104. The inverting amplifier 201 is coupled to the signal path between the sense node 104 and amplifier 105. The inverting amplifier 201 may present a high impedance input, like the amplifier 105, and thus the MEMS sensor may operate in a constant charge mode as described above. The voltage signal from the sense node 104 may be used as a first input signal $V_{INP}$ for amplifier 105. The inverting amplifier 201 also generates a signal $V_{INN}$ which is complementary and inverted version of the signal $V_{INP}$, i.e. an antiphase signal. The antiphase signal $V_{INN}$ is provided as a second input signal to the amplifier 105 and is also coupled to the bias capacitor $C_{BIAS}$. This signal $V_{INN}$ is thus coupled through the $C_{BIAS}$ capacitor to the first plate of the MEMS sensor $C_{MEMS}$. The voltage variation $V_{SIG}$ due to a variation of the separation of the plates or electrodes of MEMS sensor $C_{MEMS}$ is thus imposed on the inverted signal $V_{INN}$ with a result that $V_{SIG}$ becomes the differential voltage between the two input signals $V_{INP}$ and $V_{INN}$. As such each input signal $V_{INP}$ and $V_{INN}$ is half the magnitude, for a given signal voltage variation $V_{SIG}$, compared to the single-ended input version described with reference to FIG. 1.

The differential input signal level is thus equal to $V_{INP}-V_{INN}$ and has substantially double the input range compared to the single-ended input signal $V_{IN}$.

This increase in linear operating range not only increases the range of sound pressure level (SPL) that can be detected accurately, but the increased operating range available may allow for a greater freedom in the design of various system parameters such as transducer sensitivity and amplifier gain, which can allow for a reduction in overall noise.

However the inverting amplifier 201 will itself be an additional source of noise which can introduce noise into the output signal.

Figure 3A:
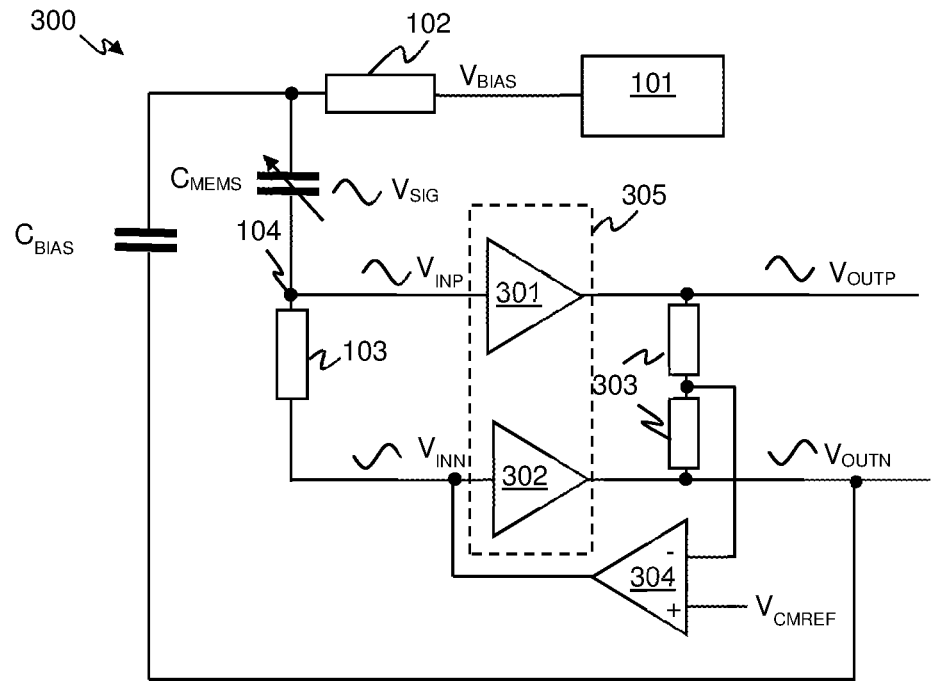
FIGS. 3a and 3b illustrate MEMS sensor arrangements according to other embodiments.

FIG. 3a illustrates another embodiment in which an antiphase signal generator generates the antiphase signal from a common mode output feedback signal. In this embodiment a first single-ended low-noise amplifier (LNA) 301 receives the signal from the sense node 104 as a first input signal $V_{INP}$ and amplifies this signal to provide the output signal $V_{OUTP}$. A second single-ended LNA 302 is arranged to amplify the generated antiphase signal $V_{INN}$ to provide an output signal $V_{OUTN}$. The two outputs are connected on either side of resistances 303 and the midpoint voltage between these resistances is tapped as a common-mode voltage. Amplifier 304 is arranged in a feedback path between the common-mode tap point and the input to the LNA 302. Amplifier 304 receives the feedback common-mode voltage and a reference $V_{CMREF}$. This feedback path, in effect, tries to maintain the common-mode voltage to be a constant value based on $V_{CMREF}$. Amplifier 304 may be relatively high gain amplifier and thus drives the output $V_{OUTN}$ of LNA 302 to be the inverse of the output of LNA 301 so as to maintain the common-mode voltage. Thus the output $V_{OUTN}$ of LNA 302 is complementary to and the inverse of, i.e. in antiphase, the output $V_{OUTP}$ from LNA 301. The common-mode feedback amplifier 304 can thus be seen as the antiphase signal generator.

The output voltage signal $V_{OUTN}$ is fed back to the first plate MEMS sensor $C_{MEMS}$ via the capacitance $C_{BIAS}$ in a similar fashion as described above with reference to FIG. 2 in order that the voltage variation $V_{SIG}$ appears as a differential voltage $V_{INP}-V_{INN}$.

Figure 3B:
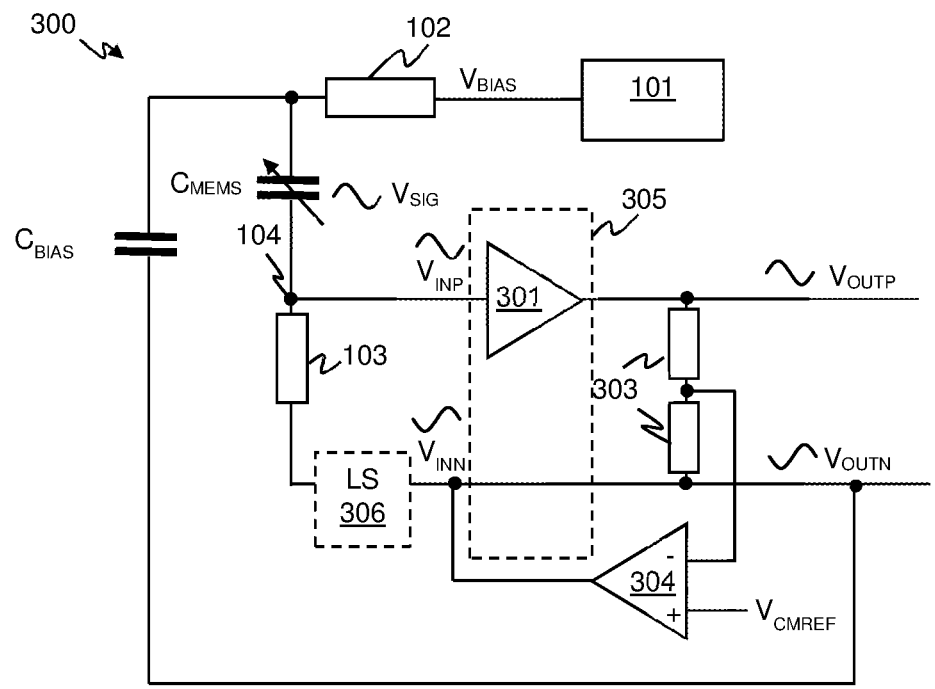

Any noise introduced by LNA 302 is suppressed through the action of the feedback path including the common-mode feedback amplifier 304. That is, the LNA 302 in FIG. 3a is within a feedback loop for the common-mode feedback amplifier 304. In some implementations this may relax the requirements on size and/or current of LNA 302 for a desired noise performance. In some embodiments there may not be a need for LNA 302 to amplify or buffer the generated antiphase signal. FIG. 3b illustrates an embodiment similar to that illustrated in FIG. 3a but where the LNA 302 is omitted. The output of the common-mode feedback amplifier 304 drives the negative signal path and thus the antiphase signal $V_{INN}$ may be used to provide the output signal $V_{OUTN}$ without requiring any buffering etc.

Where the LNA 301 for the first input signal $V_{INP}$ comprises a PMOS follower, a level shift block 306 may be provided to level shift the generated antiphase signal down to the input DC bias voltage level for DC biasing purposes.

The common-mode feedback amplifier 304 may thus be used to generate an antiphase signal which may drive, substantially directly, a second signal path for the antiphase signal output, e.g. the output of the common-mode feedback amplifier 304 may be directly coupled to an input node of the amplifier arrangement for the antiphase signal. In some instances an LNA or buffer 302 or may be included in the second signal path for the antiphase signal, within the feedback loop for the common-mode feedback amplifier 304, but in some instance buffering of the antiphase signal generated by common-mode feedback amplifier 304 may not be necessary.

Noise introduced by the common-mode feedback amplifier 304 and/or arising on the reference $V_{CMREF}$ will appear as common mode noise only and may be readily rejected by downstream components receiving the output signals $V_{OUTP}$ and $V_{OUTN}$, e.g. an audio codec or the like.

Note that the embodiment illustrated in FIG. 3a shows two single-ended LNAs 301 and 302 as providing the functionality of a differential-input/differential-output amplifier arrangement 305. In some embodiments a differential amplifier could be used instead of the two LNAs 301 and 302, although the suppression of noise associated with $V_{OUTN}$ may not be as good.

FIG. 4 illustrates one example of how the embodiment of FIG. 3a may be implemented in more detail, showing just the amplifier arrangement 400. The LNAs 301 and 302 are each implemented comprising PMOS source followers, with Class-AB output drivers 401 and 402 respectively arranged to close the feedback loops to drive the outputs $V_{OUTP}$ and $V_{OUTN}$. The use of Class-AB output drivers 401 and 402 to close the feedback loops provides a super source follower configuration which improves linearity and drive strength.

There is however a secondary noise effect due to the capacitance of the gate-drain of the PMOS 403 of the LNA 301 as illustrated with respect to FIG. 5a. LNA 302, if present, does not create this effect due to the low impedance at $V_{INN}$.

FIG. 5a illustrates the LNA 301 implemented as a super-source follower, thus including additional MOS 501, and also including the Class-AB output driver 401 discussed above. FIG. 5a illustrates the gate-drain capacitance of the PMOS 403 as a separate capacitance $C_{GD}$ for explanation. It can be seen that this gate-drain capacitance $C_{GD}$ is effectively connected in series with the capacitance of the MEMS sensor $C_{MEMS}$ and thus these two capacitances form a potential divider. Any common-mode noise at the drain with respect to the gate of PMOS 403 will thus be seen as a signal component at the gate, which will thus be represented in the output signal $V_{OUTP}$ In contrast, the gate-drain capacitance $C_{GD}$ of LNA 302 does not form a capacitive potential divider with the input sensor so it does not convert common mode noise to an input signal. Thus common mode noise may be converted to noise in the differential signal.

To mitigate this effect the drain of the PMOS 403 may be bootstrapped to the output signal as illustrated in FIG. 5b. In this embodiment the gate of MOS 501 is driven by the output signal, possibly after some level shift voltage $V_{LS}$ is applied for optimising the voltage headroom. This results in a signal, which is in-phase with the input signal, being applied to the drain of PMOS 403 which eliminates the conversion of common-mode noise to the input signal.

This also has the effect of making the input capacitance of the LNA 301 to appear to be nil, which reduces signal attenuation and can allow a larger PMOS to be used than otherwise would be the case, with a resultant reduction in flicker noise. The input signal $V_{INP}$ would also suffer less attenuation as $C_{GD}$ is typically the dominant load capacitance.

Figure 5C:
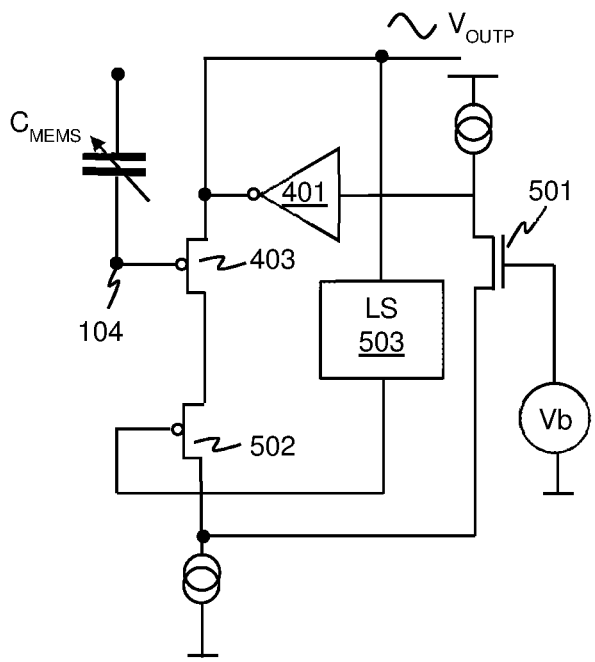

FIG. 5c illustrates the LNA 301 implemented as a super-source follower in a similar fashion as illustrated in FIG. 5a, thus including additional MOS 501 and also including the Class-AB output driver 401 discussed above. The embodiment of FIG. 5c includes a cascade device 502 which is driven with a level-shifted version of the output signal, e.g. a version of the output signal derived from the output and appropriately level shifted by level-shifter 503. This arrangement of FIG. 5c helps avoid imposing thermal or flicker noise onto the drain node of PMOS 403 which may be advantageous in some applications.

Figure 6:
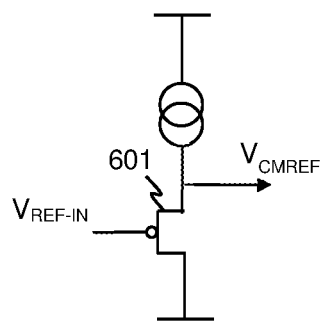
FIG. 6 illustrates one example for generating a common mode reference.

The reference voltage $V_{CMREF}$ for the common-mode feedback amplifier 304 may be generated in any convenient way. FIG. 6 illustrates that reference voltage $V_{CMREF}$ may be generated from an input reference $V_{REF-IN}$ using a replica PMOS 601 which is a scaled down copy of the input PMOS 403. The input reference $V_{REF-IN}$ may be some suitable reference, for instance a bandgap derived reference voltage.

Figure 7:
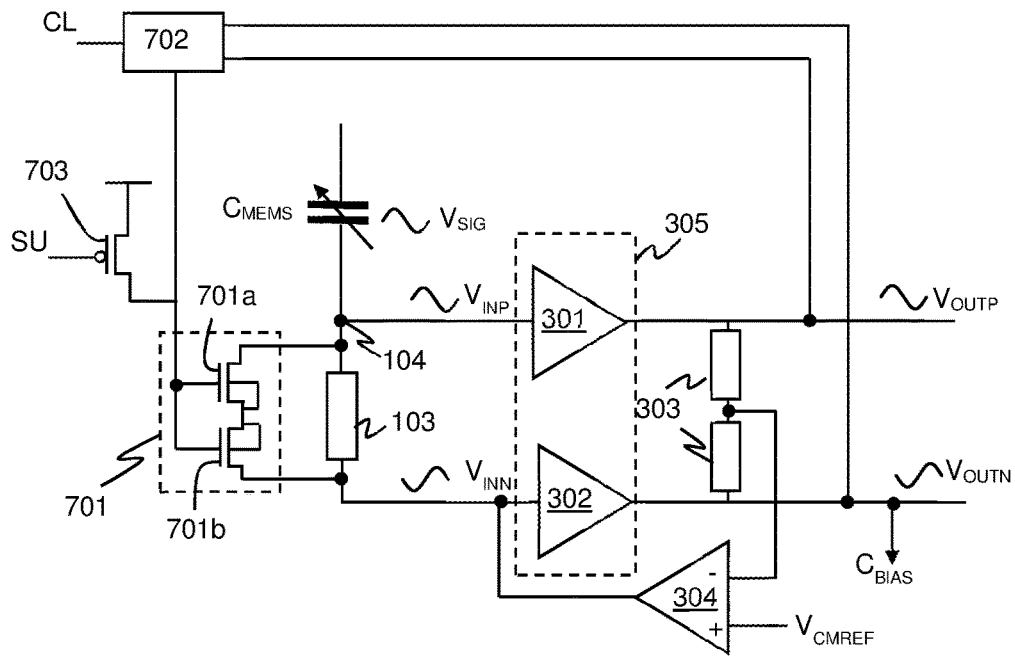
FIG. 7 illustrates an amplifier arrangement with voltage clamping.

In some embodiments the input signal, i.e. $V_{INP}$, may be voltage clamped so as to avoid the input signal, and hence the output signals, exceeding a defined voltage level. FIG. 7 illustrates an embodiment with voltage clamping.

In this embodiment the output signals $V_{OUTP}$ and $V_{OUTN}$ are monitored by clamp controller 702. Monitoring the output signal avoids the need for monitoring to be directly applied to sense node 104 and thus avoids additional leakage and capacitive loading of this node, however in other embodiments the clamp controller could monitor the signal $V_{INP}$ and/or the derived antiphase signal $V_{INN}$. Clamp controller effectively monitors the output signals against a clamp limit CL. Given that the output signals $V_{OUTP}$ and $V_{OUTN}$ are complementary signals both signals can be compared to a single clamp limit to provide both clamping for positive and negative voltage excursions. Thus a high positive voltage excursion may lead $V_{OUTP}$ to go above a positive clamp limit or $V_{OUTN}$ to drop below a negative clamp limit. Likewise a high negative voltage excursion could result in $V_{OUTN}$ going above the positive clamp limit or $V_{OUTP}$ to drop below the negative clamp limit.

In the event that either output signal exceeds the clamp limit a control signal is generated to turn on a bypass switch 701. The bypass switch provides a bypass path between the inputs for $V_{INP}$ and $V_{INN}$ that avoids the high impedance element 103. Clamp current may thus flow through the switch 701 from the $V_{INP}$ node to the $V_{INN}$ node if $V_{OUTN}$ exceeds the clamp limit and from $V_{INN}$ node to the $V_{INP}$ node if $V_{OUTP}$ exceeds the clamp limit. In this embodiment the bypass switch 701 is implemented by two series connected NMOS devices 701a and 701b with p-wells connected to the mid-point, rather than ground, to reduce leakage. The clamp controller 702 may comprise an amplifier with moderate gain to avoid stability issues.

The bypass switch 701 may also be used at start-up of the sensor arrangement to allow for rapid charging of the sensor apparatus to the operating voltages/charge levels and thus avoid the long time constants associated with the high impedance element 103. A start-up control 703 may thus be responsive to a start-up signal SU to activate the bypass switch 701.

Using the bypass switch 701 for both rapid start-up and also for voltage clamping also reduces the number of components connected to the sense node 104, compared with separate bypass and clamping arrangements, and thus also helps to reduce leakage and loading at the sense node 104.

There may also be a start-up bypass switch associated with the voltage biasing path for biasing the first plate of the MEMS sensor $C_{MEMS}$. The bypass switch associated with the biasing path may provide a bypass path across impedance 102. As noted above however in embodiments of the present disclosure the biasing node for biasing the MEMS sensor $C_{MEMS}$ may, in use, experience a signal component, e.g. $V_{INN}$ or $V_{OUTN}$ which is fed back via the biasing capacitor $C_{BIAS}$. This can impact on the operation of a bypass switch.

Figure 8A:
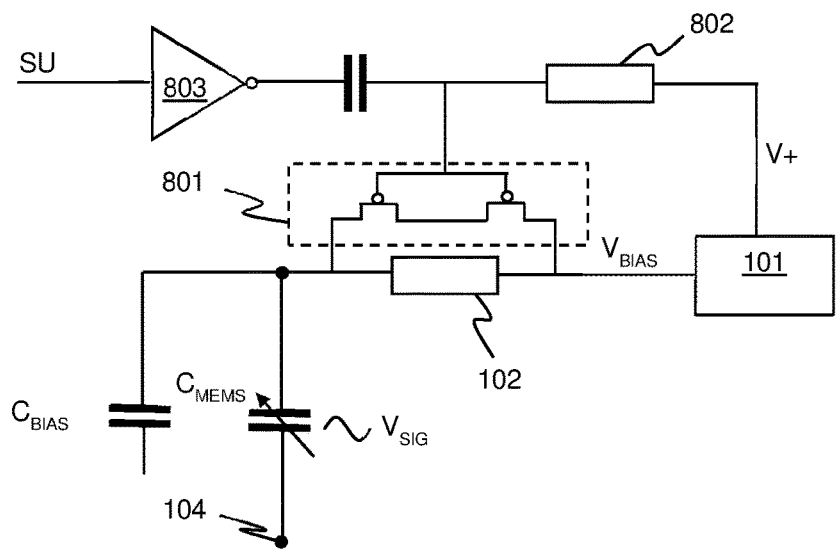
FIGS. 8a and 8b illustrate example of biasing circuitry.

FIG. 8a illustrates one example of a biasing arrangement with a suitable biasing bypass switch 801. In this example the biasing bypass switch 801 may comprise series connected PMOS devices providing a bypass path across impedance 102. The voltage source 101, e.g. a charge pump, provides, in normal operation, the bias voltage $V_{BIAS}$ via impedance 102. To ensure that the bypass switch remains turned off in normal operation, given the signal component applied to the biasing node via the biasing capacitor $C_{BIAS}$, the voltage source may also provide a voltage V+ which is higher than the bias voltage $V_{BIAS}$ and which is applied to the gate(s) of the switch 801 via a resistor 802. This higher voltage V+ should be sufficiently higher than the biasing voltage that the bypass switch 801 remains off in normal operation for the expected operating conditions. For a typical MEMS sensor the higher voltage V+ may be of the order of 1V or so higher than the biasing voltage $V_{BIAS}$. For start-up operation controller 803 responds to a start-up control SU to bring the gate voltage of the biasing bypass switch 801 down to turn the switch on and provide a bypass path for rapid charging of the MEMS sensor $C_{MEMS}$.

Figure 8B:
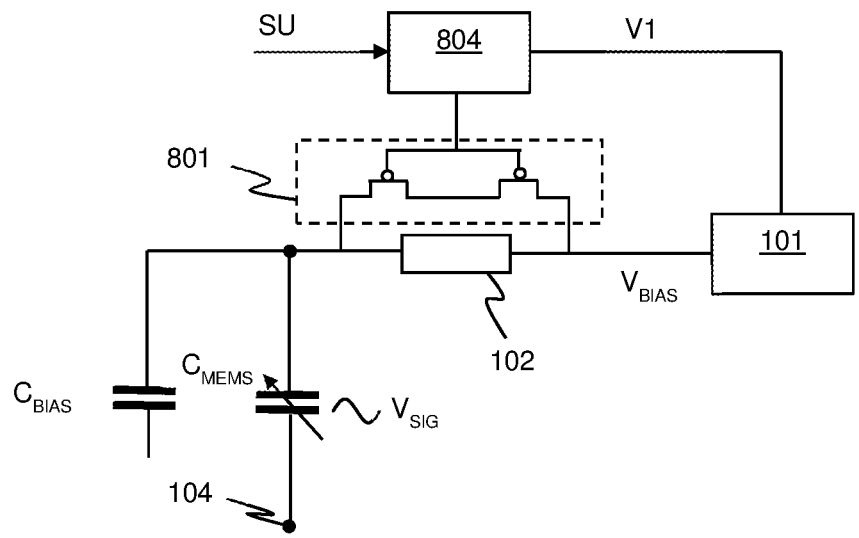

FIG. 8b illustrates an alternative example of a biasing arrangement with a bypass switch 801. In the example illustrated in FIG. 8b the gate control signal for controlling the bypass switch 801 is generated by one or more additional charge pump stages 804. The charge pump 101 may, for example, be a Dickson type charge pump and the additional charge pump stages may comprise one or additional stages of the charge pump that can be selectively activated or deactivated by the start-up control signal SU. The voltage input V1 to the additional stages may be derived from the penultimate or previous stage so that the voltage V1 input to the additional stage(s) 804 is lower than the bias voltage. In normal operation the additional stages may be activated to that the voltage supplied to the bypass switch is higher than the bias voltage $V_{BIAS}$ to ensure the bypass switch remains off in operation. During start-up the additional stage(s) 804 are deactivated and the lower voltage V1 is supplied to the bypass switch. It will be appreciated that although shown as two separate block in FIG. 8b for clarity the function of charge pump 101 and additional stage(s) 804 could be implemented by one charge pump with outputs from appropriate pump stages.

As noted previously the derived differential signal $V_{OUTN}$ (or $V_{INN}$) may be fed back to the biasing node of the MEMS sensor $C_{MEMS}$ via the biasing capacitor $C_{BIAS}$. This effectively provides level shifting of the bias voltage, such that that full scale voltage variation $V_{SIG}$ is provided as the differential voltage. In some embodiments however the bias voltage could instead be level shifted appropriately by some suitable feedback from one of the differential signals, e.g. $V_{OUTN}$ (or $V_{INN}$), to control the voltage source 101, for example using a charge pump.

Figure 9:
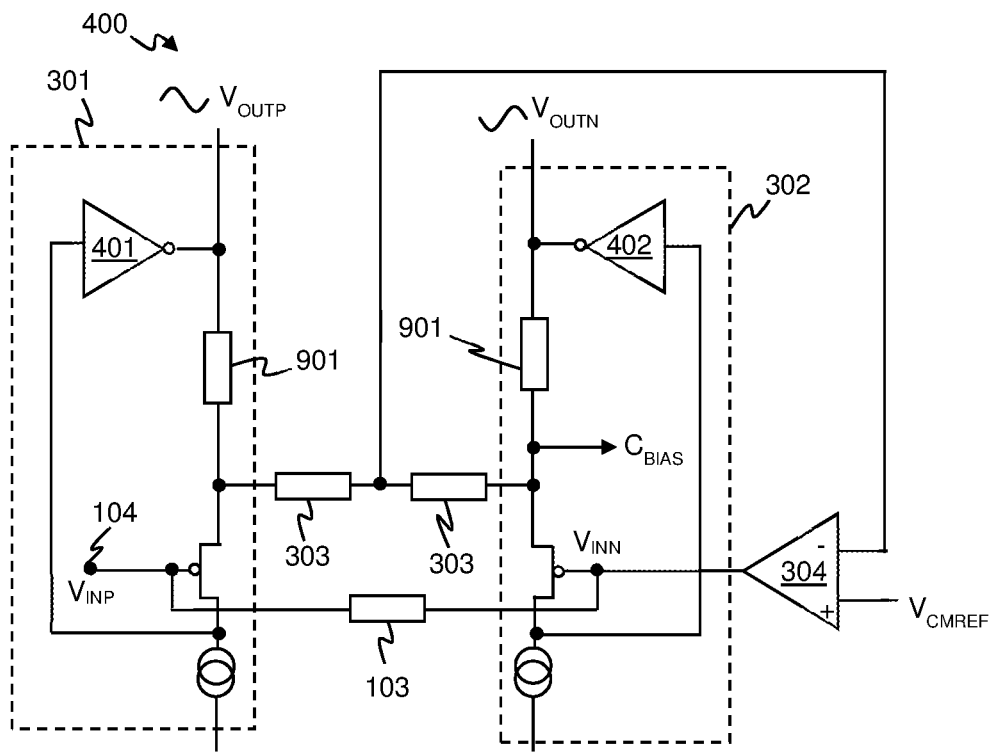
FIG. 9 illustrates an amplifier arrangement with gain.

FIG. 9 illustrates a further example of amplifier arrangement that includes gain. FIG. 9 illustrates an amplifier arrangement that is similar to that illustrated in FIG. 4 which operates in generally the same way. However the arrangement of FIG. 9 includes resistors 901 which result in voltage gain being applied to the output signals. As noted previously the class AB feedback around the PMOS of LNAs 301 and 302 provide super-source-follower behaviour so that the PMOS operates at the constant current of the current source and thus a signal dependent current flows through resistors 303. The same current will flow through additional resistors 901 and thus the relevant output voltage is gained up by a factor of $1+(R_{901}/R_{303})$ where $R_{901}$ is the resistance of the resistor 901 and $R_{303}$ is the resistance of the resistor 303. This allows voltage gain to be applied to the signal (assuming that there is sufficient headroom) at the front end of the MEMS amplifier arrangement, which can relax noise constraints for a subsequent stage in the signal processing path and in some instances could allow for some gain trimming, e.g. to account for part-to-part variations in sensitivity to be compensated. It will be noted that the antiphase signal applied to the biasing node via $C_{BIAS}$ is tapped from the source of the PMOS and thus this signal sees unity gain from the input $V_{INN}$.

Embodiments of the present disclosure thus provide amplifier arrangements for MEMS capacitive sensors that provide good linearity and noise performance over a relatively large operating range by deriving an antiphase signal to the received input signal and using an amplifier arrangement with differential inputs and differential outputs.

Embodiments are particularly applicable to readout circuitry for MEMS capacitive transducers, and especially to MEMS microphones. However the principles may be applied to sensing signals from other transducers or other types of sensors. Embodiments may be arranged as part of an audio and/or signal processing circuit, for instance an audio circuit which may be provided in a host device. Embodiments of the invention also relate to MEMS or similar capacitive ultrasonic transducer circuits. A circuit according to an embodiment of the present invention may be implemented as an integrated circuit. A MEMS transducer may form part of the integrated circuit on a monolithic substrate or be connected to the integrated circuit in use.

Embodiments may be implemented in a host device, especially a portable and/or battery powered host device such as a mobile telephone, an audio player, a video player, a PDA, a mobile computing platform such as a laptop computer or tablet and/or a games device for example.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

The invention claimed is:

1. An amplifier apparatus for amplifying an input signal from a MEMS capacitive sensor comprising:
   a sense node for receiving the input signal;
   an antiphase signal generator for generating a second signal which is in antiphase with the input signal; and
   an amplifier arrangement configured to receive the input signal at a first input and the second signal at a second input and to output corresponding first and second output signals,
   wherein the antiphase signal generator generates the second signal based on a common-mode voltage of the first and second output signals.

2. An amplifier arrangement as claimed in claim 1 further comprising biasing circuitry for generating a bias voltage for biasing the MEMS capacitive sensor at a biasing node wherein the amplifier arrangement is configured to modulate the bias voltage at the bias node with a modulation signal based on the second signal.

3. An amplifier arrangement as claimed in claim 2 comprising a feedback path for feeding the second signal or the second output signal back to the biasing node.

4. An amplifier arrangement as claimed in claim 3 wherein said feedback path comprises a biasing capacitor.

5. An amplifier apparatus as claimed in claim 1 wherein the antiphase signal generator comprises a feedback amplifier configured to receive a common-mode signal indicative of a common mode voltage of the first and second output signals and a common-mode reference voltage and to drive the second signal at the second input of amplifier arrangement to keep the common mode voltage of the first and second output signals to be equal to the common-mode reference voltage.

6. An amplifier apparatus as claimed in claim 5 comprising first and second resistances connected in series between a first output node driven with the first output signal and a second output node driven with the second output signal, wherein the common-mode signal is derived from the midpoint of the first and second resistances.

7. An amplifier apparatus as claimed in claim 5 comprising a common-mode reference generator for generating the common-mode reference voltage based on an input reference voltage, wherein the common-mode reference generator comprises a transistor which is a scaled replica of an input transistor of the amplifier arrangement.

8. An amplifier apparatus as claimed in claim 1 wherein the antiphase signal generator comprises an inverting amplifier configured to receive the input signal from the sense node.

9. An amplifier apparatus as claimed in claim 1 wherein the amplifier arrangement comprises a first single-ended amplifier for amplifying the input signal.

10. An amplifier apparatus as claimed in claim 9 wherein the amplifier arrangement further comprises a second single-ended amplifier for amplifying the second signal.

11. An amplifier apparatus as claimed in claim 9 wherein the first amplifier comprise an input transistor with a gate terminal connected to the sense node and a bootstrap circuit for driving a drain terminal of the input transistor in phase with the first output signal.

12. An amplifier apparatus as claimed in claim 1 comprising an input bypass switch for connecting the first input of the amplifier arrangement to the second input.

13. An amplifier apparatus as claimed in claim 12 further comprising clamp controller for selectively controlling the input bypass switch to clamp the input signal within a defined voltage range.

14. An amplifier apparatus as claimed in claim 13 wherein the clamp controller is configured to monitor at least one of the input signal, the first output signal and the second output signal against a clamp limit.

15. An amplifier arrangement as claimed in claim 12 wherein the apparatus is configured to close said input bypass switch in response to a start-up control signal.

16. An amplifier arrangement as claimed in claim 2 wherein said biasing circuitry comprises a voltage source for outputting the bias voltage and a resistance between the voltage source and the biasing node and comprising a biasing bypass switch for providing a bypass path that bypassing the resistance between the voltage source and the biasing node.

17. An amplifier arrangement as claimed in claim 16 wherein the voltage source is also configured to generate a control voltage, the control voltage being higher than the bias voltage, wherein the biasing circuitry is configured such that, in normal operation the control voltage is applied to a gate terminal of the biasing bypass switch.

18. An amplifier apparatus for amplifying an input signal from a MEMS capacitive sensor comprising:
 an amplifier arrangement having first and second inputs;
 wherein the first input is configured to receive the input signal and the second input is configured to receive a second signal which is in antiphase with the input signal;
 a signal generator for generating the second signal at said second input; and
 a bias source for biasing the MEMS capacitive sensor with a bias voltage;
 wherein the bias voltage is modulated based on the second signal,
 wherein the signal generator generates the second signal based on a common-mode voltage of first and second output signals of the amplifier arrangement.

19. An amplifier arrangement for amplifying an input signal from a MEMS capacitive sensor comprising:
 a first single-ended input amplifier configured to receive and amplify the input signal as a first output signal;
 a second single-ended input amplifier configured to receive and amplify a second signal as a second output signal;
 wherein the second signal is generated by the amplifier arrangement to be in antiphase to the first signal; and
 a modulator for modulating a bias voltage applied to the MEMS capacitive sensor based on said second signal,
 wherein the second signal is generated by the amplifier arrangement based on a common-mode voltage of the first and second output signals.

20. An amplifier apparatus for amplifying an input signal from a MEMS capacitive sensor comprising:
 a sense node for receiving the input signal;
 an antiphase signal generator for generating a second signal which is in antiphase with the input signal; and
 an amplifier arrangement configured to receive the input signal at a first input and the second signal at a second input and to output corresponding first and second output signals,
 wherein the antiphase signal generator comprises a feedback amplifier configured to receive a common-mode signal indicative of a common mode voltage of the first and second output signals and a common-mode reference voltage and to drive the second signal at the second input of the amplifier arrangement to keep the common mode voltage of the first and second output signals to be equal to the common-mode reference voltage.

21. An amplifier apparatus as claimed in claim 20 comprising first and second resistances connected in series between a first output node driven with the first output signal and a second output node driven with the second output signal, wherein the common-mode signal is derived from the midpoint of the first and second resistances.

22. An amplifier apparatus as claimed in claim 20 comprising a common-mode reference generator for generating the common-mode reference voltage based on an input reference voltage, wherein the common-mode reference generator comprises a transistor which is a scaled replica of an input transistor of the amplifier arrangement.

23. An amplifier apparatus for amplifying an input signal from a MEMS capacitive sensor comprising:
 an amplifier arrangement having first and second inputs;
 wherein the first input is configured to receive the input signal and the second input is configured to receive a second signal which is in antiphase with the input signal;
 a signal generator for generating the second signal at said second input; and
 a bias source for biasing the MEMS capacitive sensor with a bias voltage;
 wherein the bias voltage is modulated based on the second signal,
 wherein the signal generator comprises a feedback amplifier configured to receive a common-mode signal indicative of a common mode voltage of first and second output signals of the amplifier arrangement and a common-mode reference voltage and to drive the second signal at the second input of the amplifier arrangement to keep the common mode voltage of the first and second output signals to be equal to the common-mode reference voltage.

24. An amplifier apparatus as claimed in claim 23 comprising first and second resistances connected in series between a first output node driven with the first output signal and a second output node driven with the second output signal, wherein the common-mode signal is derived from the midpoint of the first and second resistances.

25. An amplifier apparatus as claimed in claim 23 comprising a common-mode reference generator for generating the common-mode reference voltage based on an input reference voltage, wherein the common-mode reference generator comprises a transistor which is a scaled replica of an input transistor of the amplifier arrangement.

26. An amplifier arrangement for amplifying an input signal from a MEMS capacitive sensor comprising:
  a first single-ended input amplifier configured to receive and amplify the input signal as a first output signal;
  a second single-ended input amplifier configured to receive and amplify a second signal as a second output signal;
  wherein the second signal is generated by the amplifier arrangement to be in antiphase to the first signal; and
  a modulator for modulating a bias voltage applied to the MEMS capacitive sensor based on said second signal,
  wherein the second single-ended input amplifier comprises a feedback amplifier configured to receive a common-mode signal indicative of a common mode voltage of the first and second output signals and a common-mode reference voltage and to drive the second signal at the second input of the amplifier arrangement to keep the common mode voltage of the first and second output signals to be equal to the common-mode reference voltage.

27. An amplifier apparatus as claimed in claim 26 comprising first and second resistances connected in series between a first output node driven with the first output signal and a second output node driven with the second output signal, wherein the common-mode signal is derived from the midpoint of the first and second resistances.

28. An amplifier apparatus as claimed in claim 26 comprising a common-mode reference generator for generating the common-mode reference voltage based on an input reference voltage, wherein the common-mode reference generator comprises a transistor which is a scaled replica of an input transistor of the amplifier arrangement.

* * * * *